(12) United States Patent
Misaka et al.

(10) Patent No.: US 11,534,094 B2
(45) Date of Patent: Dec. 27, 2022

(54) BRAIN RESPONSE MEASUREMENT SYSTEM, BRAIN RESPONSE MEASUREMENT METHOD, AND BRAIN RESPONSE MEASUREMENT PROGRAM

(71) Applicants: Yoshihiro Misaka, Ishikawa (JP); Hirofumi Morise, Kanagawa (JP); Kiwamu Kudo, Ishikawa (JP)

(72) Inventors: Yoshihiro Misaka, Ishikawa (JP); Hirofumi Morise, Kanagawa (JP); Kiwamu Kudo, Ishikawa (JP)

(73) Assignee: Ricoh Company, Ltd., Tokyo (JP)

( * ) Notice: Subject to any disclaimer, the term of this patent is extended or adjusted under 35 U.S.C. 154(b) by 369 days.

(21) Appl. No.: 16/809,762

(22) Filed: Mar. 5, 2020

(65) Prior Publication Data
US 2020/0289008 A1    Sep. 17, 2020

(30) Foreign Application Priority Data
Mar. 13, 2019  (JP) .............................. JP2019-046411

(51) Int. Cl.
*A61B 5/246* (2021.01)
*A61B 5/00* (2006.01)
*A61N 2/00* (2006.01)

(52) U.S. Cl.
CPC ............ *A61B 5/246* (2021.01); *A61B 5/4064* (2013.01); *A61N 2/006* (2013.01)

(58) Field of Classification Search
CPC ........ A61B 5/4064; A61B 5/246; A61N 2/006
See application file for complete search history.

(56) References Cited

U.S. PATENT DOCUMENTS 8,838,247 B2 *  9/2014  Hagedorn .............. A61B 5/375
                                                                607/45
9,241,652 B2     1/2016  Adachi et al.
(Continued)

FOREIGN PATENT DOCUMENTS

JP      4028549 B2 *  12/2007  ........... A61B 5/0482
JP      5249478         7/2013
(Continued)

OTHER PUBLICATIONS

Raij et al., "Onset timing of cross-sensory activations and multisensory interactions in auditory and visual sensory cortices", Eur J Neurosci. May 2010, 31(10), 1772-1782.
(Continued)

*Primary Examiner* — Vinh T Lam
(74) *Attorney, Agent, or Firm* — IPUSA, PLLC

(57) ABSTRACT

A brain response measurement system includes a stimulation timing control unit calculating, based on a delay time from a brain response to first stimulation in a first brain area to a brain response to a second stimulation in the first brain area, and a delay time from a brain response to the second stimulation in the second brain area to a brain response to the first stimulation in the second brain area, start and end times of the first stimulation and start and end times of the second stimulation that cause the brain response to the first stimulation in the first brain area and the brain response to the second stimulation in the first brain area not to overlap and cause the brain response to the second stimulation in the second brain area and the brain response to the first stimulation in the second brain area not to overlap.

16 Claims, 15 Drawing Sheets

(56) References Cited

U.S. PATENT DOCUMENTS

| | | | |
|---|---|---|---|
| 2013/0324880 A1 | 12/2013 | Adachi et al. | |
| 2015/0080753 A1 | 3/2015 | Miyazaki et al. | |
| 2019/0143073 A1* | 5/2019 | Grossman | G16H 10/00 |
| | | | 600/28 |
| 2019/0150768 A1* | 5/2019 | Pradeep | G16H 20/70 |
| 2019/0200912 A1 | 7/2019 | Morise et al. | |

FOREIGN PATENT DOCUMENTS

| | | |
|---|---|---|
| JP | 5352029 | 11/2013 |
| JP | 2014-133080 | 7/2014 |
| JP | 2015-066043 | 4/2015 |
| JP | 2019-118536 | 7/2019 |
| JP | 2019-162278 | 9/2019 |
| WO | 2019/181753 | 9/2019 |

OTHER PUBLICATIONS

Lam et al., "Effects of visual and auditory stimulation on somatosensory evoked magnetic fields", Clinical Neurophysiology 110 (1999) 295-304.

* cited by examiner

FIG.6

| PATTERN | GROUP | CONDITION 1 | CONDITION 2 |
|---|---|---|---|
| (a) | Gr1 | $0 \leq t2s < t1s$ | $t2e < t1s < t1e < \delta a + t2s$ |
| (b) | | | $t1s \leq t2e < t1e < \delta a + t2s$ |
| (c) | | | $t1e \leq t2e < \delta b + t1s$ |
| (d) | Gr2 | $t2s = t1s$ | $t2e < t1e < \delta a + t2s$ |
| (e) | | | $t1e \leq t2e < \delta b + t1s$ |
| (f) | Gr3 | $t1s \leq t2s < t1e$ | $t2e < t1e < \delta a + t2s$ |
| (g) | | | $t1e \leq t2e < \delta b + t1s$ |
| (h) | Gr4 | $t1e \leq t2s$ | $t2e < \delta b + t1s$ |

BRAIN RESPONSE MEASUREMENT SYSTEM, BRAIN RESPONSE MEASUREMENT METHOD, AND BRAIN RESPONSE MEASUREMENT PROGRAM

CROSS-REFERENCE TO RELATED APPLICATIONS

This application is based on and claims priority to Japanese Patent Application No. 2019-046411, filed on Mar. 13, 2019, the entire contents of which are incorporated herein by reference.

BACKGROUND OF THE INVENTION

Field of the Invention

The present invention relates to a brain response measurement system, a brain response measurement method, and a brain response measurement program.

Description of the Related Art

MEG (Magnetoenephalograph), which is one of brain response measurement systems, is a device for measuring and analyzing a weak biomagnetic field generated by human brain nerve activity. In the measurement of the biological magnetic field by the brain response measurement system, nerve activity is induced by external stimulation such as visual stimulation and auditory stimulation, and the magnetic field generated by nerve activity is measured repeatedly by the sensor to reduce the effect of noise by summing and averaging.

A method of presenting auditory stimulation while presenting images is proposed (Japanese Pat. No. 5352029) in order to suppress variations in auditory event-related potentials resulting from changes in the arousal of a subject due to repeated auditory stimulation. On the other hand, in order to prevent the visual response from being mixed into the acoustic event-related response, a method of not applying an auditory stimulation for a predetermined period when the brightness of the image changes significantly due to a change in the image scene is proposed (Japanese Patent No. 5249478).

Generally, when auditory stimulation is applied to a subject, a brain response is induced in the auditory cortex of the brain, followed by a brain response in a region different from that of the auditory cortex. Similarly, visual stimulation of a subject induces a brain response in the visual cortex of the brain, followed by a brain response in a region different from that of the visual cortex. Brain responses in the auditory and visual cortices can be distinguished by using a measurement device with a high spatial resolution.

However, when the subject is given the auditory and the visual stimulation in parallel, for example, in order to shorten the measurement time of the brain responses, there may be overlap between an auditory brain response caused by the visual stimulation and an auditory brain responses caused by the visual stimulation. When the brain responses caused by multiple different stimulation overlap in a measurement object, it is impossible to measure the brain response of the measurement object to the stimulation of interest even by using a measurement device with a high spatial resolution.

SUMMARY OF THE INVENTION

A brain response measurement system includes a first stimulation output unit that applies first stimulation to a subject, a second stimulation output unit that applies second stimulation to the subject, a stimulation timing control unit that sets a timing of applying the first stimulation from the first stimulation output unit to the subject and the timing of applying the second stimulation from the second stimulation output unit to the subject, and a measurement unit that measures a brain response occurring in a first brain area of the subject and a brain response occurring in a second brain area of the subject, wherein a stimulation timing control unit calculates, based on a delay time δa from the brain response to the first stimulation in the first brain area to a brain response to the second stimulation in the first brain area, and a delay time δb from the brain response to the second stimulation in the second brain area to a brain response to the first stimulation in the second brain area, start and end times of the first stimulation and start and end times of the second stimulation that cause the brain response to the first stimulation in the first brain area and the brain response to the second stimulation in the first brain area not to overlap and cause the brain response to the second stimulation in the second brain area and the brain response to the first stimulation in the second brain are not to overlap, and wherein the calculated start and end times of the first stimulation are set to the first stimulation output unit, and the calculated start and end times of the second stimulation are set to the second stimulation output unit.

BRIEF DESCRIPTION OF THE DRAWINGS

FIG. 6 is a diagram explaining conditions that satisfy I1>0 and I2>0.

DESCRIPTION OF THE EMBODIMENTS

Figure 1:
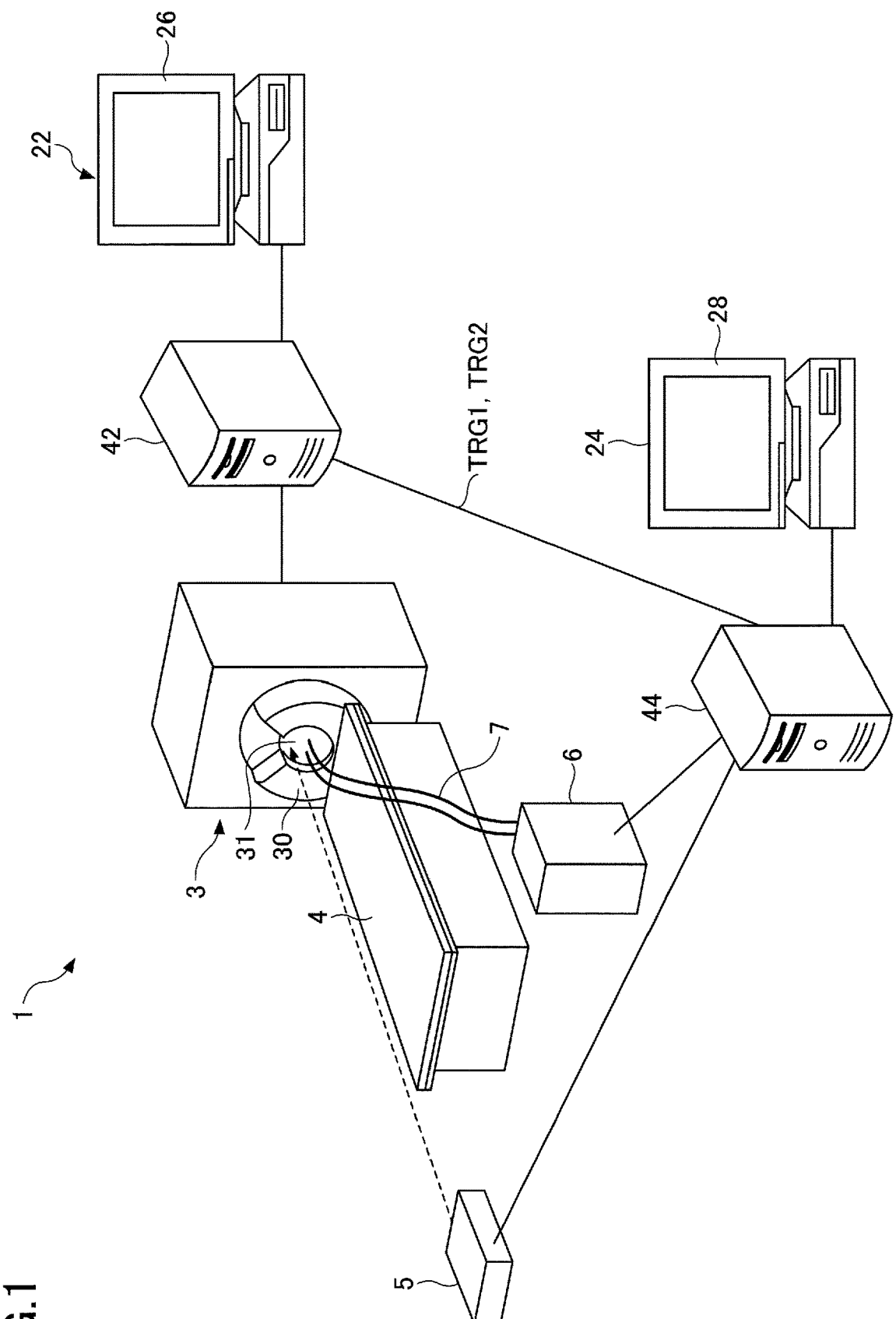
FIG. 1 is a schematic view of a biomagnetic field measurement system according to a first embodiment.

Hereinafter, embodiments will be described with reference to the figures. In each drawing, the same components are indicated by the same reference numerals and overlapping descriptions may be omitted.

First Embodiment

FIG. 1 is a schematic diagram of a biomagnetic field measurement system 1 according to a first embodiment. The biomagnetic field measurement system 1 is an example of a brain response measurement system. The biomagnetic field measurement system 1 measures, for example, a Magneto-encephalography (MEG) signal. The biomagnetic field measurement system 1 includes a measurement device 3 (brain magnetometer), a visual stimulation device 5, an auditory stimulation device 6, information processing apparatuses 42 and 44, and information display systems 22 and 24. For example, the visual stimulation device 5 includes a projector for projecting an image to a subject, and the auditory stimulation device 6 includes an audio device for generating sound. The visual stimulation device 5 is an example of the first stimulation output unit, and the auditory stimulation device 6 is an example of the second stimulation output unit.

The information processing apparatus 42 controls the measurement device 3. The information display system 22 connected to the information processing apparatus 42 includes a monitor display 26 for displaying the information of the magnetic field data obtained by the measurement device 3 and the analysis results. Here, the information processing apparatus 42 and the information display system 22 are described separately, but at least a part of the information processing apparatus 42 may be incorporated into the information display system 22.

The information processing apparatus 44 controls the visual stimulation device 5 and the auditory stimulation device 6. The information processing apparatus 44 instructs the visual stimulation device 5 and the auditory stimulation device 6 to stimulate the subject at a certain timing. The information processing apparatus 44 outputs a timing when the subject receives the stimulation from each of the visual stimulation device 5 and the auditory stimulation device 6 as trigger signals TRG1 and TRG2 (for example, time information) to the information processing apparatus 42. The information processing apparatus 42 that receives the trigger signals TRG1 and TRG2 stores the magnetic field data output from the measurement device 3 in a memory device included in the information processing apparatus 42 in association with the trigger signals TRG1 and TRG2. Synchronization by the trigger signals TRG1 and TRG2 is described later.

The measurement device 3, the information processing apparatuses 42 and 44, the visual stimulation device 5, and the auditory stimulation device 6 may be connected to each other via a network.

An information display system 24 connected to the information processing apparatus 44 may be operated, for example, by an operator of the biomagnetic field measurement system 1. The monitor display 28 of the information display system 24 may display the information necessary for an operation by an operator. At least a part of the information processing apparatus 44 may be incorporated into the information display system 24. The information display systems 22 and 24 are an example of the display device.

The subject who receives the measurement of the brain magnetic field lies on his or her back on a measuring table 4 and his or her head is placed in a dent 31 of a dewar 30 of the measurement device 3. The dewar 30 is a cryogenic holding vessel using liquid helium, and a great number of magnetic sensors for brain magnetometry are disposed inside the dent 31 of the dewar 30. The measurement device 3 collects the brain magnetic signals from the magnetic sensors and outputs the collected magnetic field signals to the information processing apparatus 42. Magnetic brain signals are collected by the measurement device 3 under the condition where a part of the subject is stimulated.

The subject whose head is inserted in the dent 31 receives visual stimulation from the image projected from the visual stimulation device 5, and receives auditory stimulation from sound from the auditory stimulation device 6 via the air tube type earphone 7 set in the ear. For example, the image from the visual stimulation device 5 is delivered to the subject through a screen (not illustrated positioned directly above the head of the subject lying on the measuring table 4 and with the side of the measurement device 3 tilted to the bottom.

The visual stimulation device 5 may include a liquid crystal display that presents an image to the subject instead of the projector. In this case, the liquid crystal display is positioned closer to the measurement device 3 than the position of the visual stimulation device 5 of FIG. 1 and far enough away from the magnetic sensor. In addition, when the liquid crystal display is positioned toward the measurement device 3, the image from the liquid crystal display may be delivered to the subject's eye via a reflecting mirror (not illustrated) positioned directly above the head of the subject lying on the measuring table 4 and with the side of the measurement device 3 tilted downward.

The measurement device 3 measures the magnetic field generated by the brain response generated in the visual cortex by the visual stimulation and the magnetic field generated by the brain response generated in the auditory cortex by the auditory stimulation. The stimulation applied to the subject is not limited to the visual and auditory stimulation, but may be visual and somatic stimulation, auditory and somatic stimulation. The visual cortex is an example of a first brain area, and the auditory cortex is an example of a second brain area.

The brain magnetic signal represents minute magnetic field variations caused by electrical activity in the brain. The brain magnetometer contained in the measurement device 3 is detected by a superconducting quantum interference device (SQUID) sensor with high sensitivity. The brain magnetometer has a high spatial resolution and can spatially separate the brain responses of multiple sensory areas by estimating a signal source of the measured data. The brain magnetometer may detect the brain magnetic field by an optically-pumped atomic magnetometer (OPAM).

Generally, the dewar 30, which incorporate the magnetic sensor, and the measuring table 4 are located in a magnetic shielding room, but for convenience of illustration, the description of the magnetic shielding room is omitted. The visual stimulation device 5 may be disposed outside the magnetic shielding room and project images from a window provided in the magnetic shielding room toward the screen or reflecting mirror. The auditory stimulation device 6 may also be disposed outside the magnetic shielding room. Preferably, the information processing apparatus 44 and the information display system 24 are disposed outside the magnetic shield room because they are operated by the operator.

Data such as the brain magnetic signal measured by the measurement device 3 and recorded in the information processing apparatus 42 are displayed as a waveform on the monitor display 26 of the information display system 22 and analyzed by the operator or the like.

Figure 2:
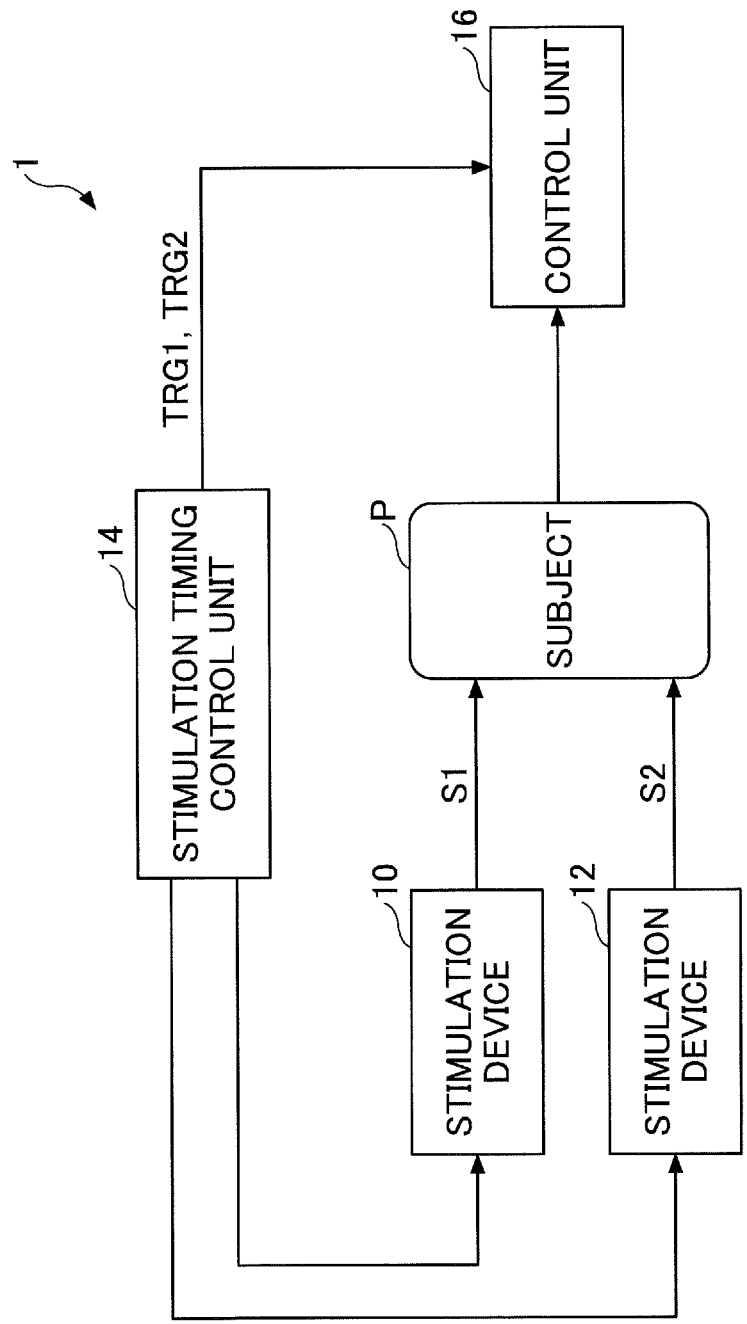
FIG. 2 is a block diagram illustrating an example of a functional configuration of the biomagnetic field measurement system.

FIG. 2 illustrates an example of the functional configuration of the biomagnetic field measurement system 1 in FIG. 1. The biomagnetic field measurement system 1 includes the stimulation devices 10 and 12, the stimulation timing control unit 14, and a measurement unit 16 for measuring the brain response of a subject P. The measurement unit 16 corresponds to the measurement device 3, the information processing apparatus 42, and the information display system 22 of FIG. 1. The stimulation timing control unit 14 corresponds to the information processing apparatus 44 and the information display system 24 of FIG. 1.

The stimulation timing control unit 14 controls the stimulation devices 10 and 12 by setting the start time and the end time of the stimulation S1 by the stimulation device 10 and the start time and the end time of the stimulation S2 by the stimulation device 12.

The stimulation device 10 applies the stimulation S1 to the subject P and the stimulation device 12 applies the stimulation S2 to the subject P. The stimulation S1 is an example of the first stimulation and stimulation S2 is an example of the second stimulation. Although not particularly limited, the stimulation S1 is described as the visual stimulation and the stimulation S2 is described as the auditory stimulation. In this case, the stimulation device 10 corresponds to the visual stimulation device 5, and the stimulation device 12 corresponds to the auditory stimulation device 6. The measurement unit 16 measures the brain response of the subject P induced by the stimulation S1 and S2, respectively.

Before the stimulation output from the stimulation devices 10 and 12 reaches the subject P, a time lag occurs depending on the length of a stimulation transmission pathway and a transmission medium. In the visual stimulation, a delay in the stimulation S1 due to the refresh rate of the projector or the liquid crystal display occurs, and in the auditory stimulation, a delay in the stimulation S2 due to air propagation occurs.

Therefore, it is preferable to previously notify the measurement device 3 of the time lag until the stimulation reaches the subject P by some means. In this embodiment, the stimulation timing control unit 14 outputs the trigger signals TRG1 and TRG2 to the measurement unit 16. For example, the trigger signal TRG1 indicates a time lag between an output of the stimulation from the stimulation device 10 and a receipt of the stimulation by the subject P. A trigger signal TRG2 indicates the time lag between an output of the stimulation from the stimulation device 12 and a receipt of the stimulation by the subject P. The trigger signal TRG1 is an example of synchronization information indicating when the subject P receives the stimulation S1, and the trigger signal TRG2 is an example of synchronization information indicating when the subject P receives the stimulation S2.

The measurement unit 16 recognizes the time when the stimulation S1 is actually applied to the subject P based on the trigger signal TRG1 and recognizes the time when the stimulation S2 is actually applied to the subject P based on the trigger signal TRG2. Thus, the measurement unit 16 can manage a measurement time of the measured magnetic field data according to the time when the subject P actually receives the stimulation from each stimulation device 10 and 12. That is, the time of the stimulation devices 10 and 12 and the measurement unit 16 can be synchronized. As a result, the measurement unit 16 can associate the time when the subject P receives the stimulation from the stimulating devices 10 and 12 with the measurement time, such as the magnetic field data (the measurement data) output from the measurement device 3, thereby improving a diagnostic accuracy.

The stimulation timing control unit 14 may be included in the measurement unit 16. In this case, the stimulation timing control unit 14 corresponds to the information processing apparatus 42 and the information display system 22 of FIG. 1, and the biomagnetic field measurement system 1 does not need to include the information processing apparatus 44 and the information display system 24.

The measurement unit 16 instructs the stimulation device 10 to start and end the stimulation S1, instructs the stimulation device 12 to start and end the stimulation S2, and measures the brain response from the subject P.

The stimulation devices 10 and 12 and the stimulation timing control unit 14 may be included in the measurement unit 16. Again, the stimulation timing control unit 14 corresponds to the information processing apparatus 42 and the information display system 22 of FIG. 1, and the biomagnetic field measurement system 1 does not need to include the information processing apparatus 44 and the information display system 24. The measurement unit 16 sets the start time and the end time of the stimulation S1 and the start time and the end time of the stimulation S2, provides the stimulation S1 and S2 to the subject P, and functions as a brain response measurement device to measure the brain response from the subject P.

Figure 3:
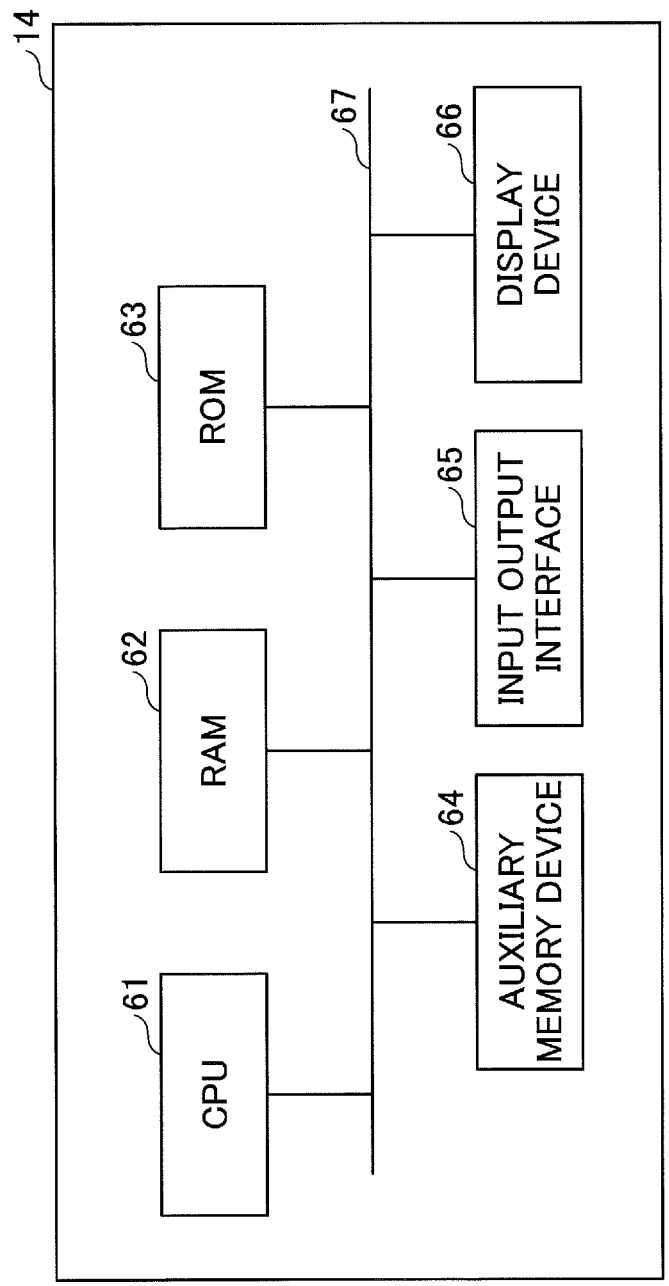
FIG. 3 illustrates an example of a hardware configuration of a stimulation timing control unit.

FIG. 3 is a diagram illustrating an example of the hardware configuration of the stimulation timing control unit 14 of FIG. 2. That is, FIG. 3 illustrates an example of the information processing apparatus 44 and the information display system 24 of FIG. 1. The information processing apparatus 42 and the information display system 22 of FIG. 1 have the same configuration as that of FIG. 3.

The stimulation timing control unit 14 includes a CPU (Central Processing Unit) 61, RAM (Random Access Memory) 62, ROM (Read Only Memory) 63, an auxiliary memory device 64, an input/output interface 65, and a display device 66 which are interconnected by a bus 67.

The CPU 61 controls the overall operation of the stimulation timing control unit 14 and performs various information processing. The CPU 61 controls the stimulation devices 10 and 12 by executing a brain response measurement program stored in ROM 63 or the auxiliary memory device 64. The RAM 62 is used as a work area of the CPU 61 and may include a non-volatile RAM for storing major control parameters and information. The ROM 63 stores various programs and parameters used in various programs. The brain response measurement program of the present invention may also be stored in the ROM 63. The auxiliary memory device 64 is a storage device such as an SSD (Solid State Drive) and an HDD (Hard Disk Drive). For example, the auxiliary memory device 64 stores a control program such as an OS (Operating System) for controlling the operation of the stimulation timing control unit 14 and various data and files necessary for the operation of the stimulation timing control unit 14. The scope of the present invention does not include transitory signals and waveforms.

The input output interface 65 includes both a user interface, such as a touch panel, a keyboard, a display screen, an operation button, and the like, and a communication interface that captures information from various sensors or information processing apparatus 42 and outputs analysis information to other electronic apparatuses. The input output interface 65 transmits the start time and the end time of the stimulation to each of the stimulation devices 10 and 12 and transmits the trigger signals TRG1 and TRG2 to the information processing apparatus 42. The display device 66 corresponds to the information display system 22 of FIG. 1.

Figure 4:
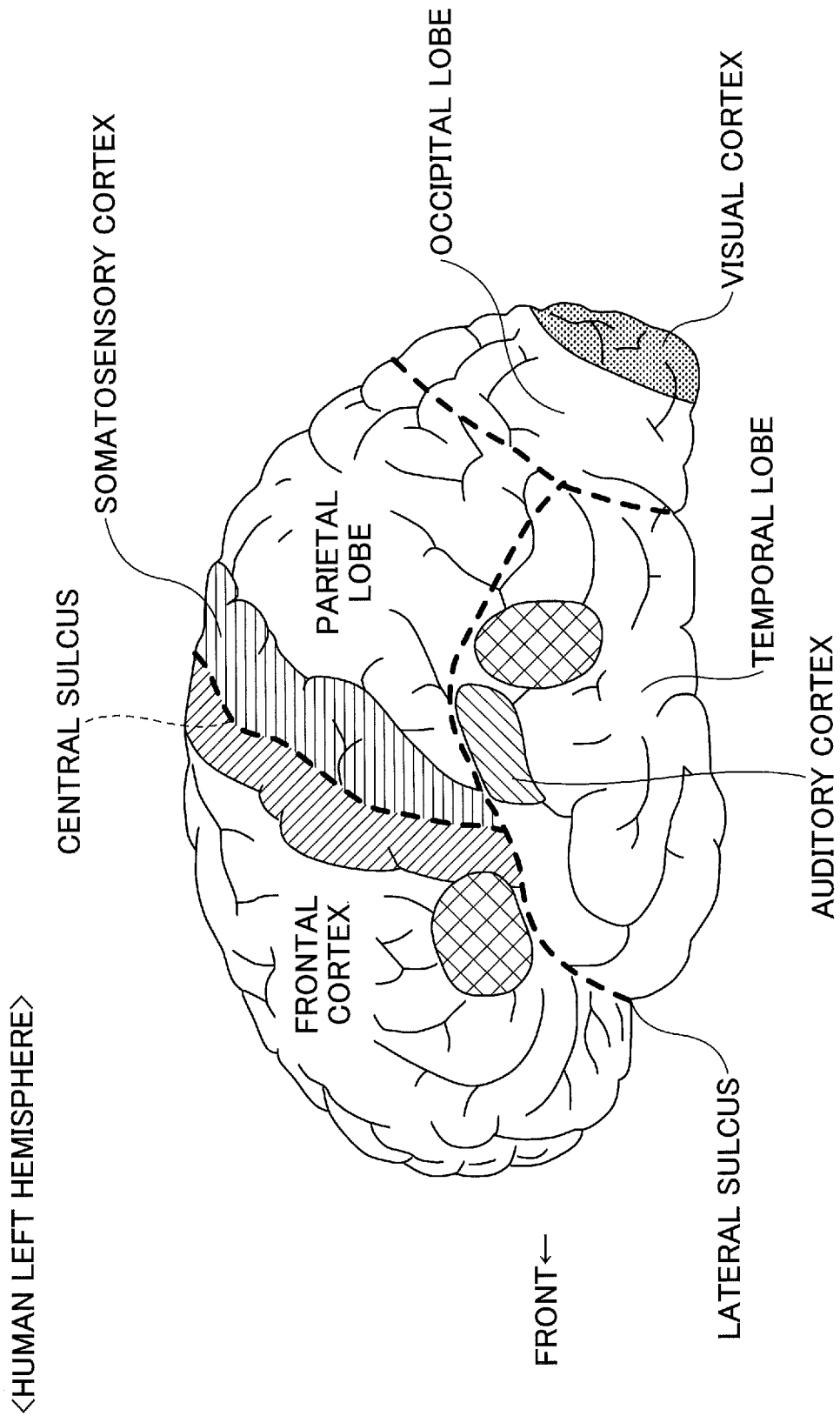
FIG. 4 illustrates a spatial arrangement of visual, auditory, and somatic cortices.

FIG. 4 is a diagram illustrating the spatial arrangement of the visual, auditory, and somatic sensation areas. FIG. 4 illustrates a human left hemisphere. The visual cortex is located on the apical side of an occipital lobe, and the auditory cortex is located on the lateral sulcus side of a temporal lobe. The somatosensory cortex is located on the central sulcus side of the parietal lobe.

Visual, auditory, and somatic sensations are all basic human sensations, and stimulation of vision, hearing, and somatic sensations is useful for examining the nervous basis of the human brain. As illustrated in FIG. 4, the visual cortex, auditory cortex, and somatic sensation cortex are spatially separated. For this reason, a brain magnetometer with a high spatial resolution can estimate the signal source from brain response generated by each stimulation and spatially separate the brain responses of the visual cortex, auditory cortex, and somatic sensory cortex, respectively.

Figure 5:
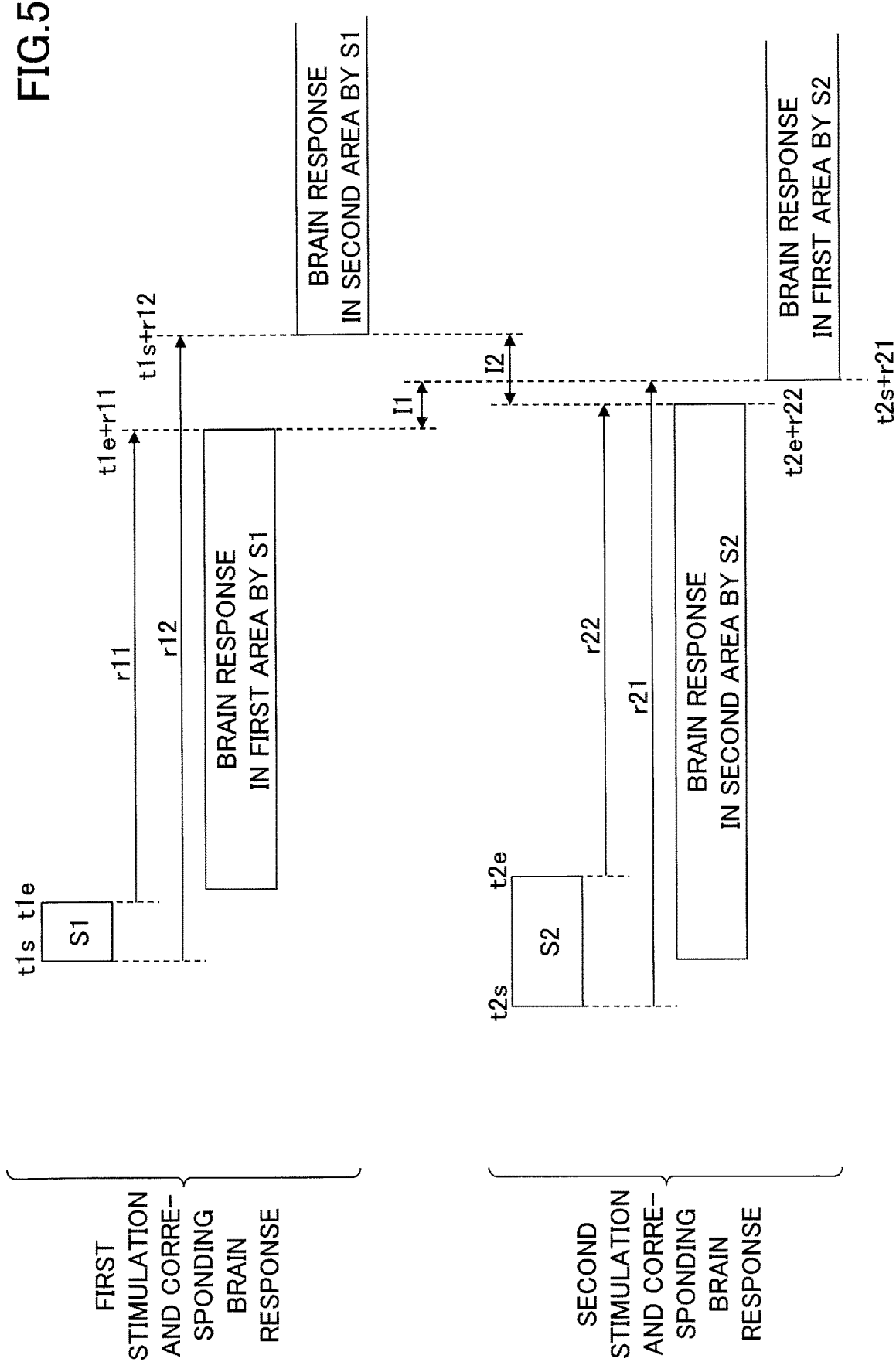
FIG. 5 illustrates definitions of timings of applying stimulation S1 and S2 to a subject and timings of brain responses in the subject responding to the stimulation S1 and S2.

FIG. 5 is a diagram illustrating the timing of applying the stimulation S1 and S2 to the subject P and the definition of the timing of the brain response of the subject P in response to the stimulation S1 and S2.

For example, the stimulation device 10 applies the stimulation S1 (e.g., visual stimulation) to the subject P from the start time t1s to the end time t1e. The stimulation S1 causes a response in the first area of the brain of the subject P (e.g., visual cortex), and the brain response in the first area lasts for a time period r11 (e.g., 150 ms) after the end time t1e of the stimulation S1. A response also appears in the second area (e.g., auditory area) of the brain of the subject P after a time period r12 (e.g., 200 ms) from the start time t1s of the stimulation S1. The time periods r11 and r12 are peculiar to the stimulation S1 and are independent of the duration of the stimulation S1. In addition, the time periods r11 and r12 may vary slightly for each subject P but the range of variation is small.

On the other hand, the stimulation device 12 applies the stimulation S2 (e.g., auditory stimulation) to the subject P from the time t2s to the time t2e. The stimulation S2 causes a response in the second area of the brain of the subject (e.g., auditory area), and the brain response in the second area lasts for a time period r22 (e.g., 150 ms) after the end time t2e of the stimulation S2. A response also appears in the first area (e.g., visual cortex) of the brain of the subject P after a time period r21 (e.g., 200 ms) from the start time t2s of the stimulation S2. The time periods r21 and r22 are peculiar to the stimulation S2 and does not depend on the duration of the stimulation S2. In addition, the time periods r21 and r22 may vary slightly for each subject P, but the variation range is small.

Figure 7:
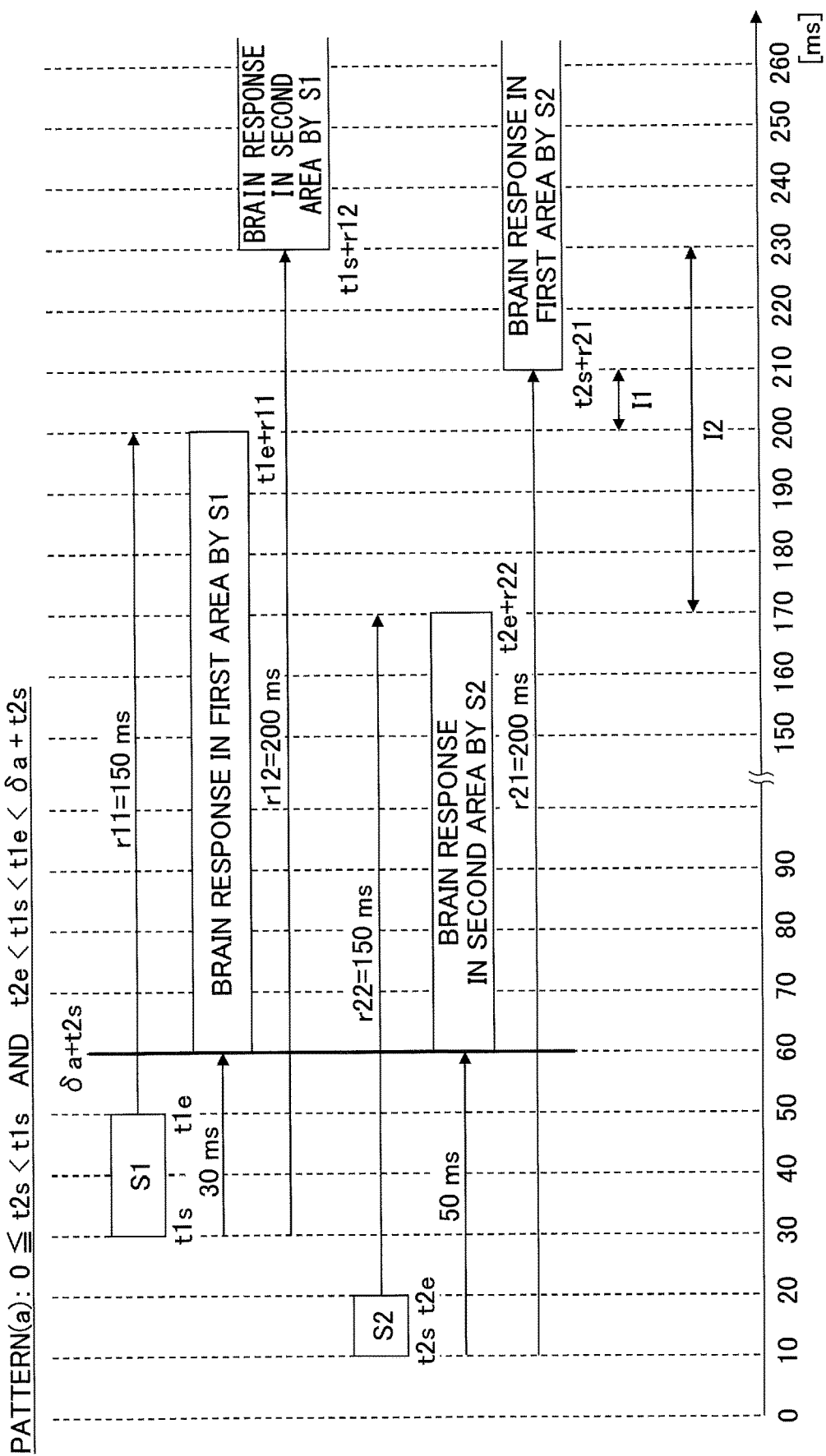
FIG. 7 illustrates an example of a stimulation timing and a brain response that satisfy conditions in pattern (a) of FIG. 6.

In FIG. 5 and FIG. 7 and the subsequent figures, which will be described later, a rectangle representing the brain response of each brain area to the stimulation is actually displayed on the monitor display 26 or the like as a waveform that attenuates with time.

Considered next is a simultaneous measurement of the magnetic field generated by the brain response generated in the first area by the stimulation S1 and the magnetic field generated by the brain response generated in the second area by the stimulation S2.

First, in order to accurately measure the magnetic field generated in the brain response in the first area by the stimulation S1, there must be no overlap between the brain response in the first area by the stimulation S1 and the brain response in the first area by the stimulation S2. Said differently, a time I1 (>0) must be maintained between the end time when the brain responds to the stimulation S1 in the first area and the start time when the brain responds to the stimulation S2 in the first area.

Similarly, in order to accurately measure the magnetic field generated by the brain response to the stimulation S2 in the second area, the brain response in the second area by stimulation S2 must not overlap with the brain response to the stimulation S1 in the second area. Said differently, the time I2 (>0) must be maintained between the end time when their brain responds to the stimulation S2 in the second area and the start time when the brain responds to the stimulation in the second area.

Therefore, by determining the times t1s, t1e, t2s, and t2e so that both of the time intervals t1 and t2 become at least "0", it is possible to simultaneously measure the brain response to the stimulation S1 in the first area and the brain response to the stimulation S2 in the second area. A time interval I1 is an example of a first time interval, and a time interval I2 is an example of a second time interval.

The time interval I1 can be expressed by Equation 1 because the end time of the brain response to the stimulation S1 in the first area "t1e+r11", and the start time of the brain response to the stimulation S2 in the first area is "t2s+r21".

[Equation 1]

$$I1 = (t2s+r21)-(t1e+r11) = (t2s-t1e)+(r21-r11) \quad (1)$$

Similarly, the time interval I2 can be expressed by Equation 2 because the end time of the brain response to the stimulation S2 in the second area is "t2e+r22", and the start time of the brain response to the stimulation S1 in the first area is "t1s+r12".

[Equation 2]

$$I2 = (t1s+r12)-(t2e+r22) = (t1s-t2e)+(r12-r22) \quad (2)$$

From the conditions I1>0 and I2>0 for simultaneously measuring the magnetic field generated by the brain response to the stimulation S1 in the first area and the magnetic field generated in the brain response to the stimulation S2 in the second area by stimulation S2, and Equations 3 and 4 are established by Equations 1 and 2, respectively.

[Equation 3]

$$(t1e-t2s) < (r21-r11) \quad (3)$$

[Equation 4]

$$(t2e-t1s) < (r12-r22) \quad (4)$$

Assuming that "r21−r11" is a time δa and "r12−r22" is a time δb, equations (3) and (4) become (5) and (6), respectively. The time δa indicates a delay time in the brain response generated in the visual cortex by the auditory stimulation due to the brain response, which is generated by the visual stimulation in the visual cortex. The time δb indicates a delay time in the brain response generated in the auditory cortex by the visual stimulation due to the brain response, which is generated by the auditory stimulation in the auditory cortex.

[Equation 5]

$$(t1e - t2s) < \delta a \quad (5)$$

[Equation 6]

$$(t2e - t1s) < \delta b \quad (6)$$

Therefore, if Equations 5 and 6 are satisfied, the time interval I1>0 and the time interval I2>0 can be satisfied. Said differently, if Equations 5 and 6 are satisfied, the brain response to the stimulation S1 in the first area and the brain response to the stimulation S2 in the first area do not overlap in time, and the brain response to the stimulation S2 in the second area and the brain response by the stimulation S1 in the second area do not overlap in time. As a result, the magnetic field generated in the brain response to the stimulation S1 in the first area and the magnetic field generated in the brain response to the stimulation S2 in the second area can be measured simultaneously.

In order to satisfy the time interval I1>0 and the time interval I2>0, the duration of the stimulation S1 and S2 should be shorter, and the difference between the start times t1s and t2s of the stimulation S1 and S2 should be smaller. However, the duration of the stimulation S1 and S2 should be no less than a minimum time to enable diagnosis of the duration and intensity of the magnetic field data generated by the brain responses in each area. That is, the duration of the stimulation S1 and S2 need to satisfy the minimum continuous time period of the stimulation S1 acquired by continuous response to the stimulation S1 in the first area for a predetermined time period and the minimum continuous time period of the stimulation S2 acquired by continuous response to the stimulation S2 in the second area for a predetermined time period, respectively.

FIG. 6 is a diagram illustrating conditions that satisfies the time interval I1>0 and the time interval I2>0. First, four groups Gr (Gr1, G 2, G 3, and Gr4) are classified in the four conditions 1, which are separated by the relationship between the start time t2s of the stimulation S2 to the stimulation S1.

The condition 1 of the group Gr1 is that the start time t2s is earlier than the start time t1s, and the condition 1 of the group Gr2 is that that the start time t2s is the same as the start time t1s. The condition 1 of the group Gr3 is that the start time t2s is the same as or later than the start time t1s and earlier than the end time t1e. The condition 1 of the group Gr4 is that the start time t2s is the same as or later than the end time t1e.

Each of the groups Gr1, Gr2, and Gr3 is classified into multiple subgroups according to the condition 2 based on the relationship between the end time t2e of the stimulation S2 and the stimulation S1 and Equations 5 or 6. The group Gr1 is classified into three subgroups, and each of the groups Gr2 and Gr3 has two subgroups, and the group Gr4 is classified into one subgroup.

Then, by satisfying both the condition 1 of each group Gr and the condition 2 of the subgroup within each group Gr, the setting specifications (patterns (a) to (h)) of the stimulation S1 and S2 that satisfy the time interval I1>0 and the time interval I2>0 can be determined. Eight patterns (a) to (h) cover conditions that satisfy time interval I1>0 and time interval I2>0.

Figure 8:
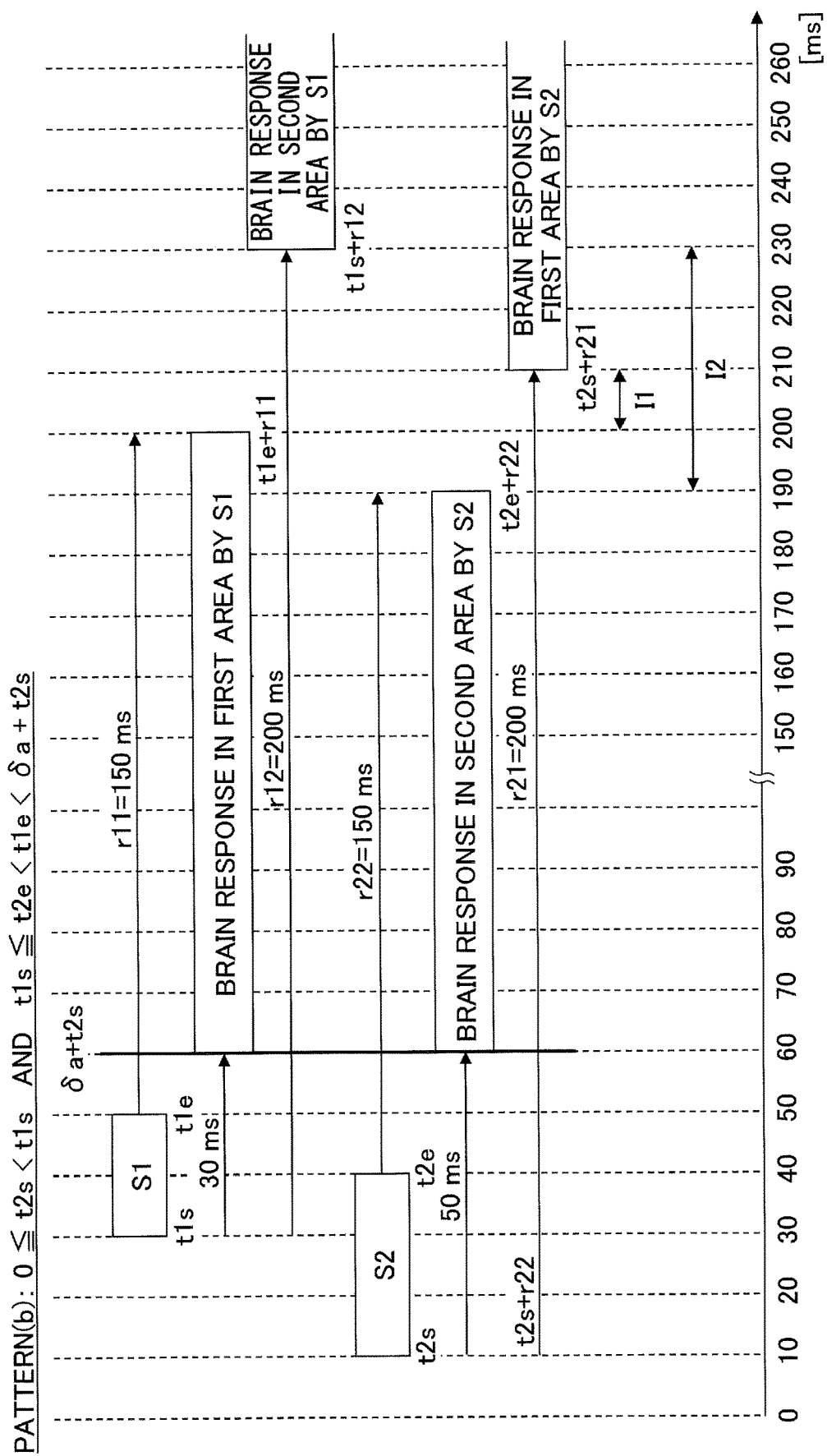
FIG. 8 illustrates an example of a stimulation timing and a brain response that satisfy conditions in pattern (b) of FIG. 6.
Figure 9:
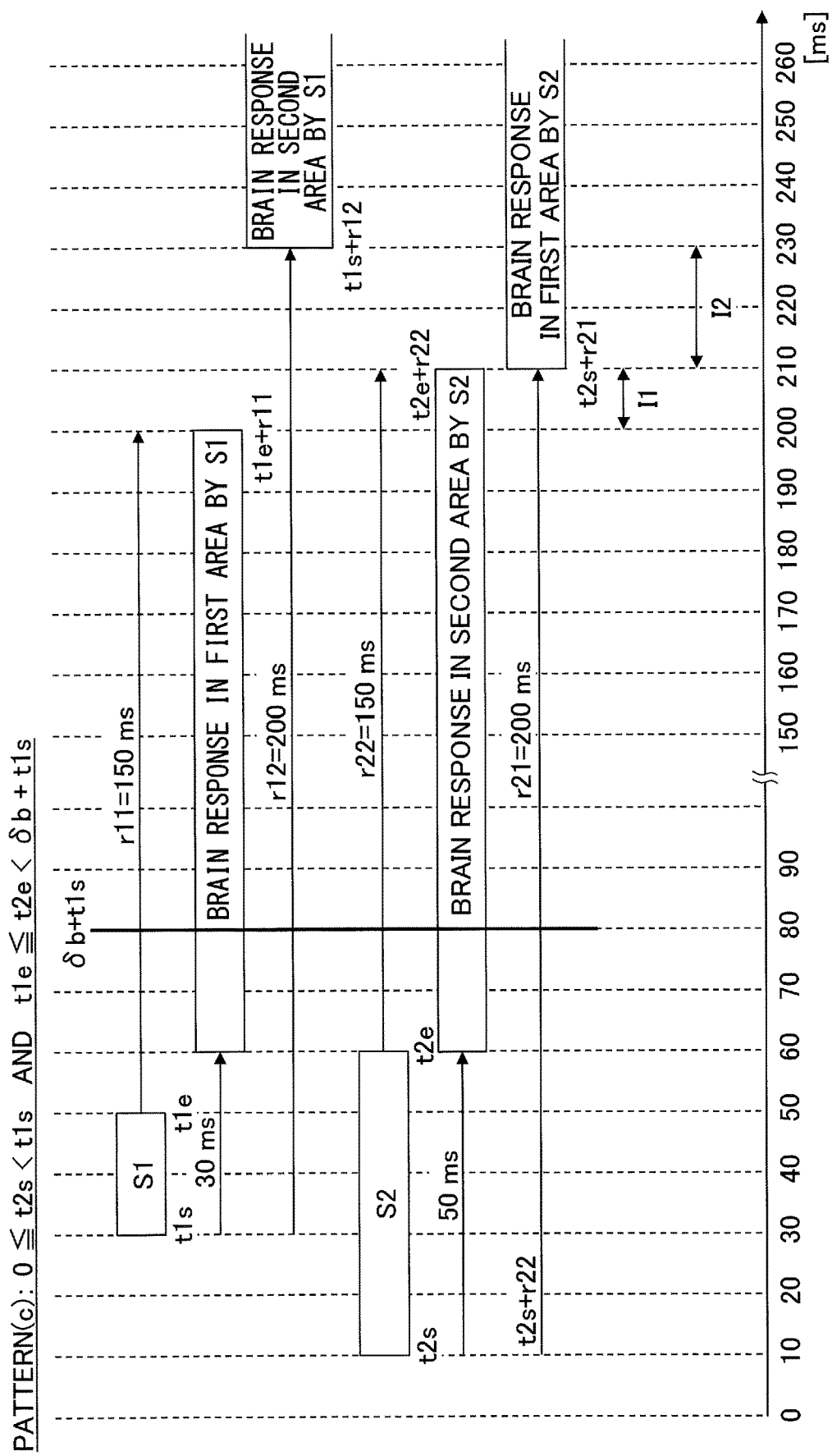
FIG. 9 illustrates an example of a stimulation timing and a brain response that satisfy conditions in pattern (c) of FIG. 6.
Figure 10:
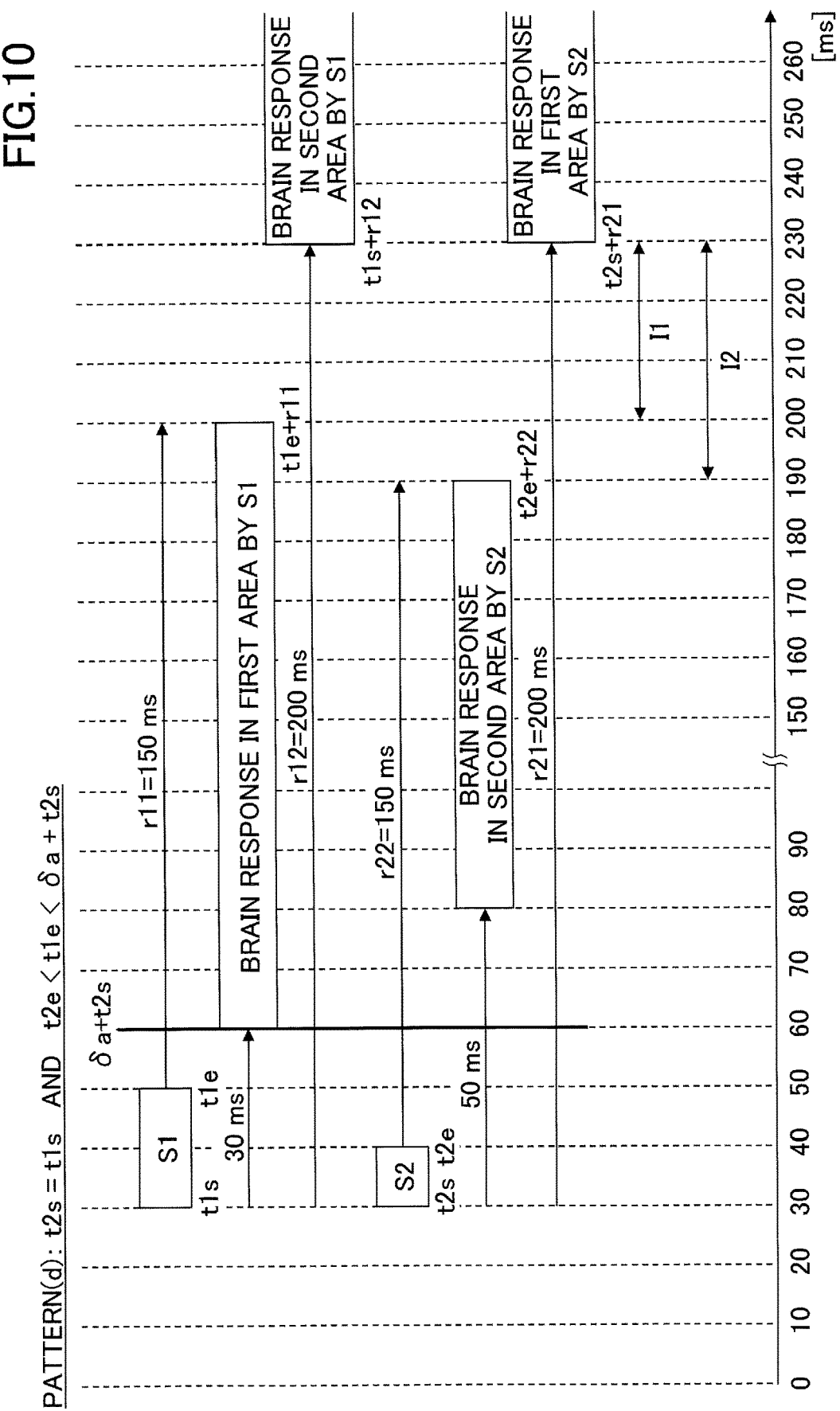
FIG. 10 illustrates an example of a stimulation timing and a brain response that satisfy conditions in pattern (d) of FIG. 6.
Figure 11:
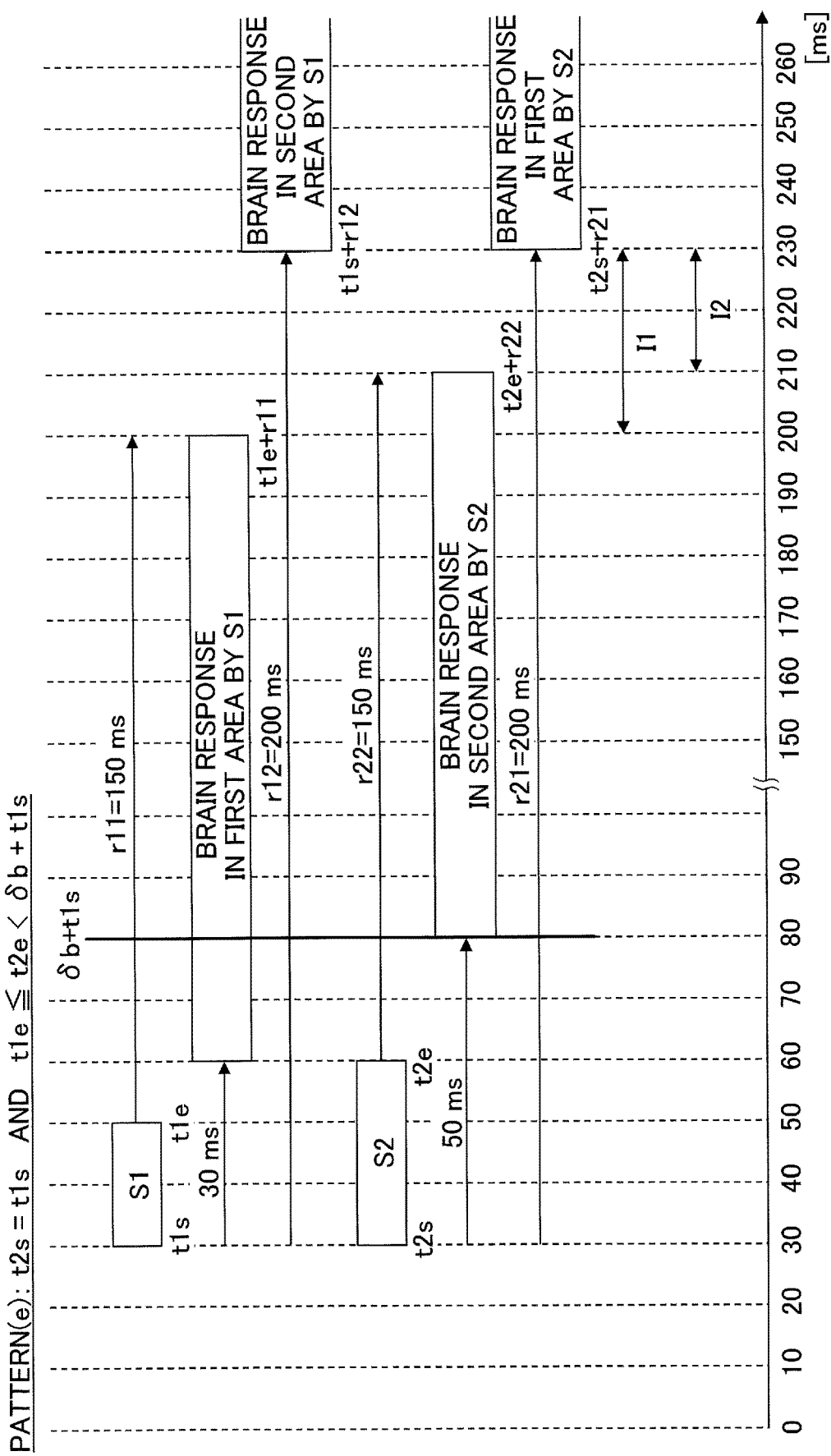
FIG. 11 illustrates an example of a stimulation timing and a brain response that satisfy conditions in pattern (e) of FIG. 6.
Figure 12:
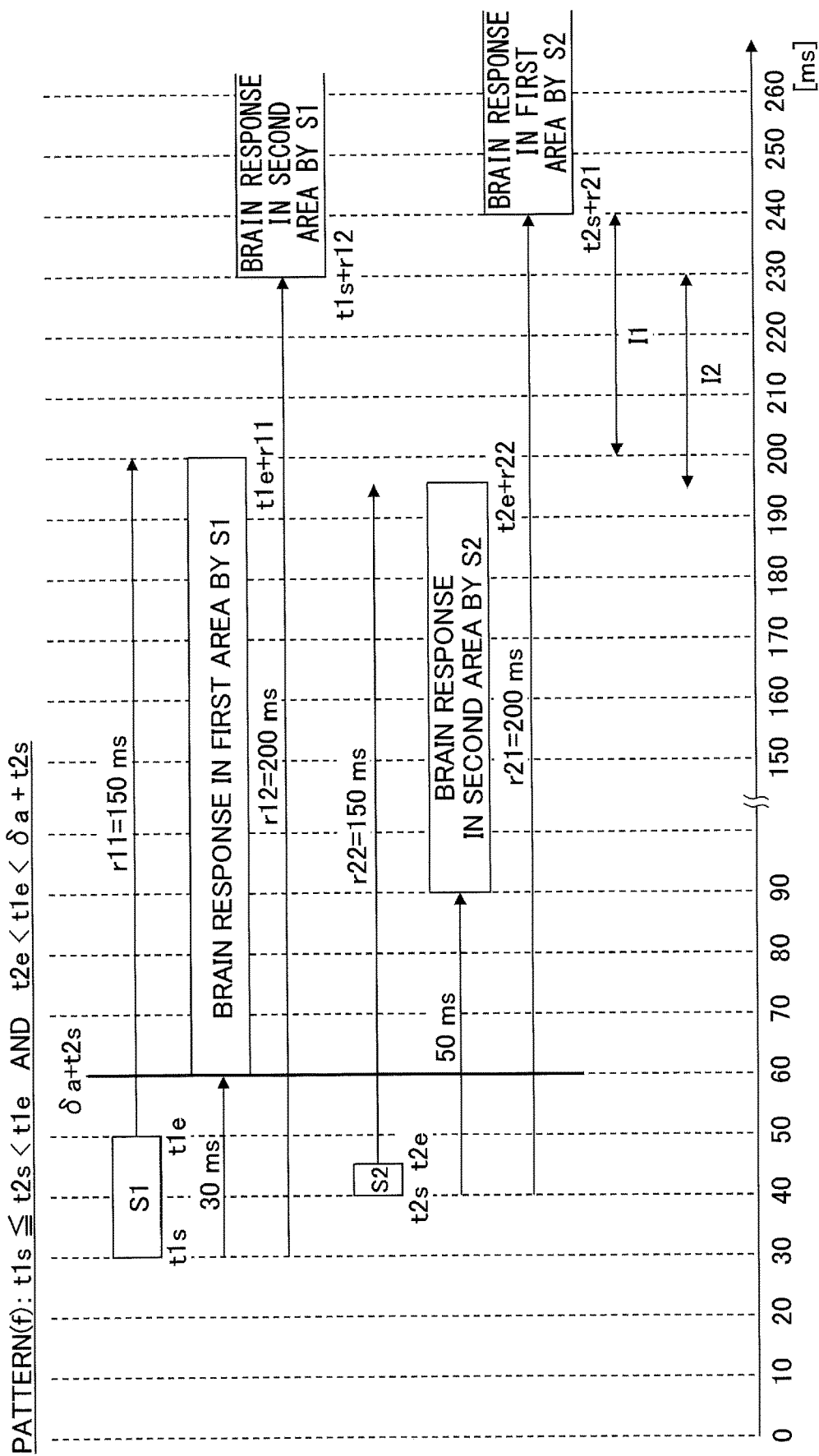
FIG. 12 illustrates an example of a stimulation timing and a brain response that satisfy conditions in pattern (f) of FIG. 6.
Figure 13:
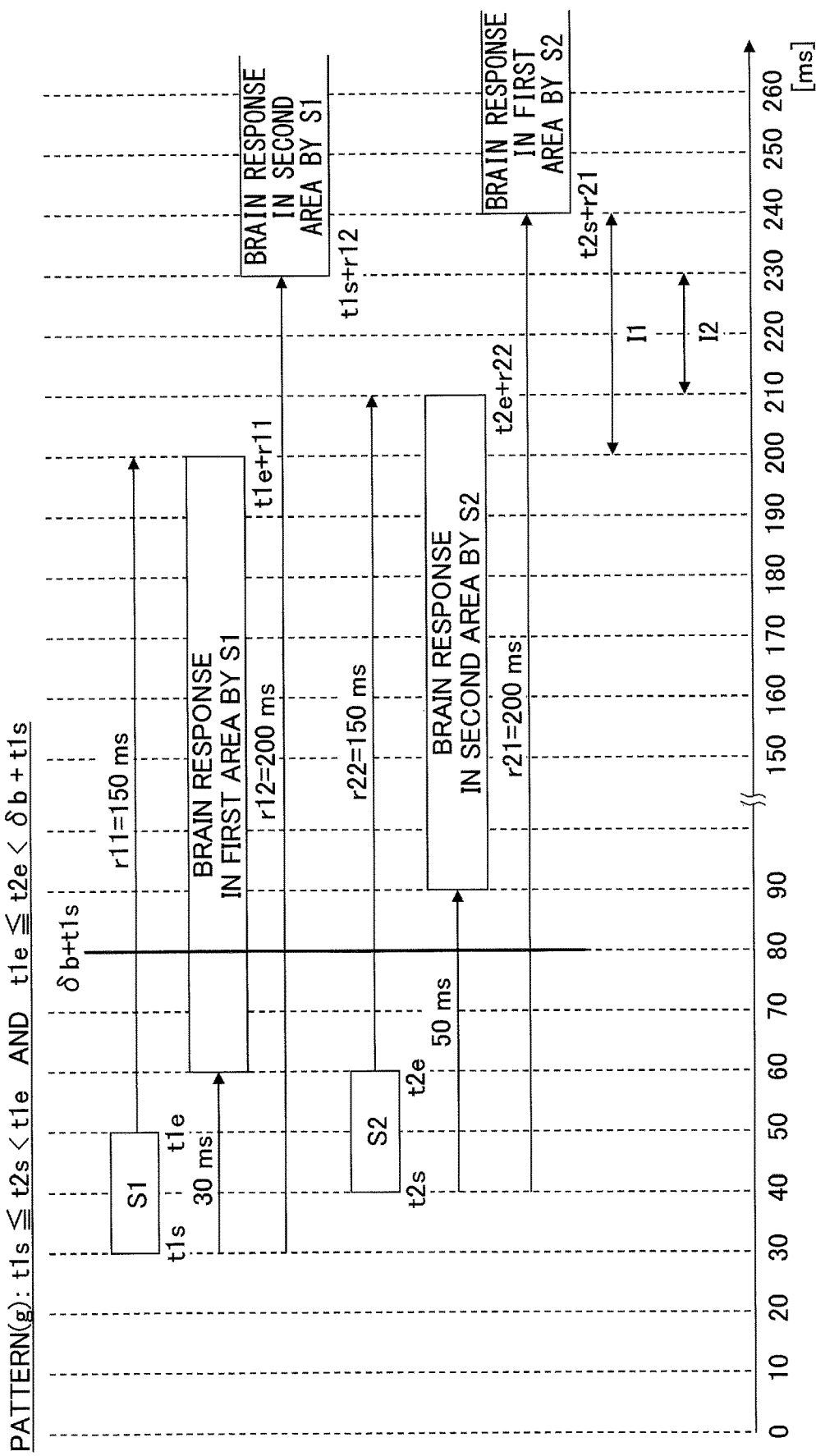
FIG. 13 illustrates an example of a stimulation timing and a brain response that satisfy conditions in pattern (g) of FIG. 6.
Figure 14:
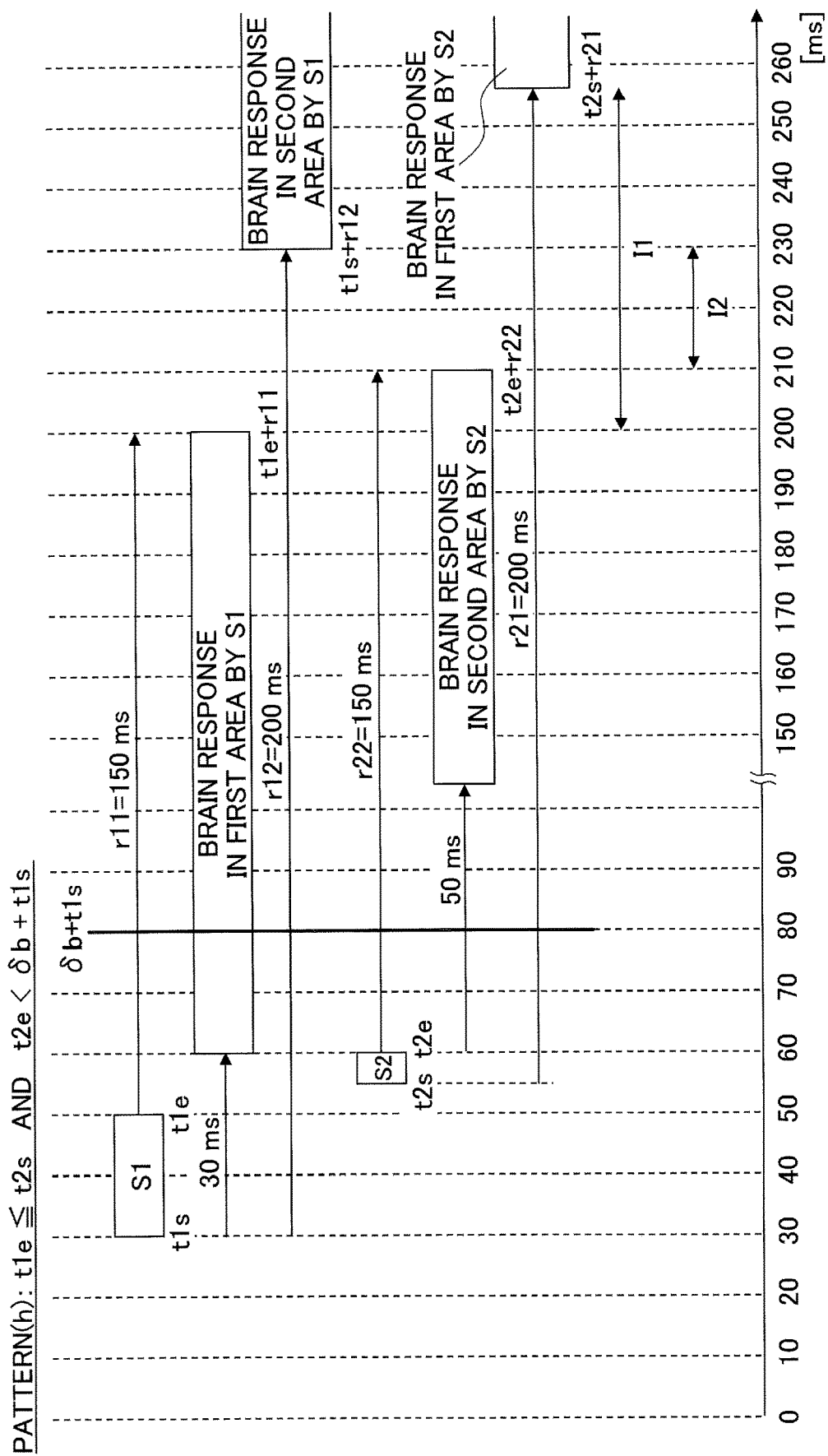
FIG. 14 illustrates an example of a stimulation timing and a brain response that satisfy conditions in pattern (h) of FIG. 6.

FIGS. 7 to 14 are diagrams illustrating examples of the stimulation S1 and S2 that satisfy the conditions of the patterns (a) to (h) in FIG. 6 and the brain responses in response to the stimulation S1 and S2, respectively. FIG. 7 illustrates an example of the stimulation timing and brain response satisfying the conditions of pattern (a) in FIG. 6, and FIG. 8 illustrates an example of the stimulation timing and brain response satisfying the conditions of pattern (b) in FIG. 6. FIG. 9 illustrates an example of the stimulation timing and brain response satisfying the conditions of pattern (c) of FIG. 6, and FIG. 10 illustrates an example of the stimulation timing and brain response satisfying the conditions of pattern (d) of FIG. 6. FIG. 11 illustrates an example of the stimulation timing and brain response satisfying the conditions of pattern (e) in FIG. 6, and FIG. 12 illustrates an example of the stimulation timing and brain response satisfying the conditions of pattern (f) in FIG. 6. FIG. 13 illustrates an example of the stimulation timing and brain response satisfying the conditions of pattern (g) of FIG. 6, and FIG. 14 illustrates an example of the stimulation timing and brain response satisfying the conditions of pattern (h) of FIG. 6.

In FIGS. 7 to 14, the time periods r11 and r22 are set to be 150 ms, and the time periods r12 and r21 are set to be 200 ms. The values of 150 ms for the time periods r11 and r22 and 200 ms for the time periods r12 and r21 are based on the brain response of the standard subject P. In this case, the delay times $\delta a$ and $\delta b$ are both 50 ms. In other words, setting $\delta a$=50 ms and $\delta b$=50 ms is desirable because it allows many subjects P to efficiently measure brain responses to different types of the stimulation. In addition, the combination of the visual stimulation S1 and the auditory stimulation S2 has a longer time to produce a brain response and a longer duration of response in the area of interest than do somatic stimulation. For this reason, the measurement efficiency improvement according to the present invention is highly effective and is a preferred combination.

In FIGS. 7 to 14, for example, the time from the start of the stimulation S1 to the onset of response in the first area is set at 30 ms, and the time from the start of the stimulation S2 to the onset of response in the second area is set to be 50 ms. The time from stimulation to response is unique for each brain area. For example, the time from the onset of the visual stimulation to the onset of the brain response in the visual cortex is about 30 to about 50 ms, the time from the onset of the auditory stimulation to the onset of the brain response in the auditory cortex is about 50 ms, and the time from the onset of the somatic sensation stimulation to the onset of the brain response in the somatic sensation cortex is about 20 ms.

That is, FIG. 7 to FIG. 14 illustrate examples of start time t1s and end time t1e of the stimulation S1 and start time t2s and end time t2e of the stimulation S2 that satisfy Equations 5 and 6 when the delay times $\delta a$ and $\delta b$ are both set to 50 ms.

The delay times $\delta a$ and $\delta b$ are not limited to 50 ms, and the values may differ from each other. The delay times $\delta a$ and $\delta b$ are previously input to the stimulation timing control 14. Before measuring the brain response of the subject P to the stimulation, the delay times $\delta a$ and $\delta b$ unique to the subject P may be specified by applying a predetermined visual and auditory stimulation to the subject P and measuring the brain response occurring in the visual and auditory cortices.

That is, the stimulation timing control unit 14 may calculate the start time t1s, the end time t1e, the start time t2s, and the end time t2e based on the delay time $\delta a$ and the delay time $\delta b$ determined in accordance with the type of the stimulation and/or characteristics of the subject P. This allows the delay times $\delta a$ and $\delta b$ to be set according to the individual brain response characteristics of the subject P, ensuring that the time intervals I1 and I2 are greater than "0".

By applying the stimulation S1 and S2 to the subject P using any of the eight patterns (a) to (h) illustrated in FIG. 6, the brain response in the visual cortex and the brain response in the auditory cortex can be measured, respectively, when the visual and auditory stimulation are applied to the subject P simultaneously, as illustrated in FIGS. 7 to 14. In other words, the brain response to the visual stimulation in the visual cortex and the brain response to the auditory stimulation in the auditory cortex can be accurately and independently detected while preventing influences of the time period during which the brain response to the auditory stimulation in the visual cortex and the time period during which the brain response to the visual stimulation in the auditory cortex from occurring.

This reduces the measurement time (i.e., the test time) of the brain response compared with a case where brain responses in the visual and auditory cortices are separately measured. Thus, brain responses in different areas induced by the stimulation in different organs can be accurately measured in a short time. As a result, the fatigue of subject P in measuring brain responses can be reduced.

By the way, the longer the time period of the stimulation (i.e., duration of stimulation) on the subject P, the longer it is possible to continue to induce the brain response over a longer time period, and more conspicuous brain response can be measured. As illustrated in patterns (d) and (e) of FIG. 6, by setting the start times t1s and t2s of the stimulation S1 and S2 to the same time, the duration of the stimulation can be increased compared with other patterns while satisfying the time interval I1>0 and the time interval I2>0. This allows the brain to continue to elicit responses for a long time period and to accurately measure a more pronounced brain response. Accordingly, patterns (d) and (e) are preferred as timing of start of the stimulation relative to other patterns. It is preferable that the duration of the stimulation be as long as possible in a range that satisfies time interval I1>0 and time interval I2>0.

In order to facilitate the measurement of brain responses, stimulation conditions may be set with consideration of the following points. In order to facilitate a detection of the brain response to the visual stimulation in the visual cortex, it is preferable that the brightness of the image given as the visual stimulation be at least 20 cd/m$^2$. Similarly, to facilitate a detection of the brain response to the auditory stimulation in the auditory cortex, sound given as the auditory stimulation preferably has sound pressure in a range from 45 dB to 65 dB. These are examples and may be set to other conditions.

In addition, the pattern of the stimulation may be varied periodically during the duration of the stimulation. For example, in the visual stimulation, the brightness of multiple rectangular regions partitioned like a grating may be periodically inverted in a staggered image pattern. In addition, the frequency or volume of sound applied to the subject P may be changed periodically in the case of an auditory stimulation. In addition, the duration of the stimulation is preferably set as long as possible within constraint condition.

Next, a preferred non-stimulation time will be described. Here, the no-stimulation time is a time period after the brain response is measured until the next stimulation is given to the subject P (i.e., a time period while no stimulation is given).

Generally, it is known that a characteristic brain response especially called an event-related potential P300 occurs 300 ms after the visual stimulation, the auditory stimulation, or the somatic sensation stimulation are applied to the subject P. The event-related potential P300 also affects the brain magnetic field. Therefore, it is preferable to insert a no-stimulation time at least 300 ms of a no-stimulation time prior to each trial to avoid overlapping of the brain response to the visual and auditory stimulation in the first trial with the brain response to the visual and auditory stimulation in the second trial.

In addition, when a constant non-stimulation time is always inserted, the start timing of the stimulation is adjusted in each trial, and the measurement device 3 measures the magnetic field information in which electrical noise, etc. reflecting the periodicity is superimposed. In this case, summed averaging does not attenuate a noise component and is detected as if the brain response had occurred. Accordingly, by randomly changing the non-stimulation time to a predetermined time range and shifting the timing of the generation of noise due to the stimulation timing, the noise component can be attenuated by the summed average, thereby allowing the brain response to be detected more accurately. As an example, it is preferable to randomly change the non-stimulation time between 700 ms and 1000 ms by estimating the time from disappearance of the brain response to a return to a baseline is 500 ms and the baseline correction section is 200 ms. Here, the baseline correction section is a time period necessary to match the reference potential of multiple magnetic sensors of a brain magnetometer.

Figure 15:
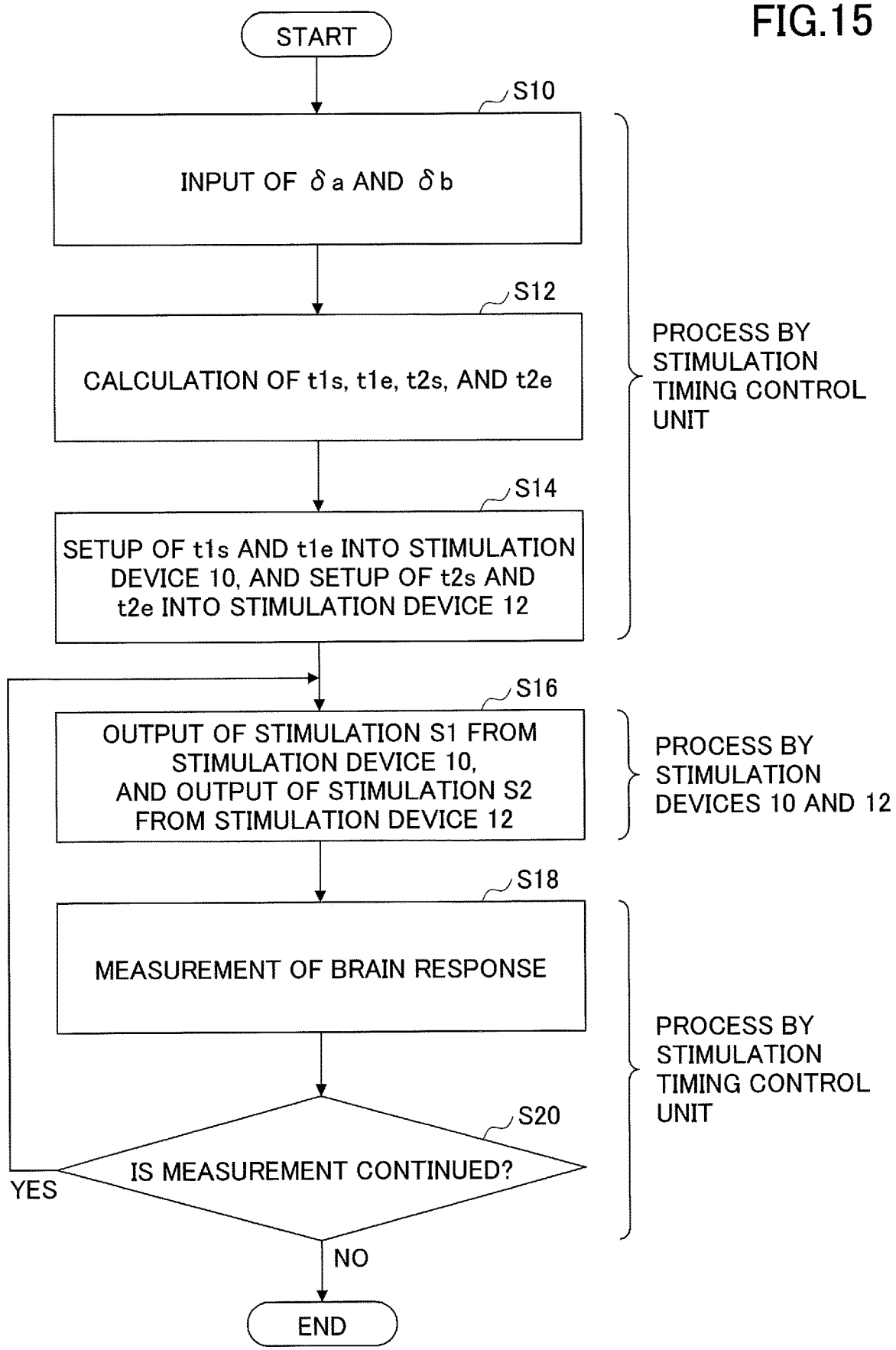
FIG. 15 is a flow diagram illustrating an example of an operation of the biomagnetic field measurement system of FIG. 1.

FIG. 15 is a flow diagram illustrating an example of an operation of the biomagnetic field measurement system 1 in FIG. 1. Said differently, FIG. 15 illustrates an example of a brain response measurement method using the biomagnetic field measurement system 1 and a brain response measurement program controlling the biomagnetic field measurement system 1. The operations of step S10, step S12, and step S14 indicate the processing performed by the stimulation timing control unit 14 in FIG. 2, and the operations of step S16 indicate the processing performed by the stimulation devices 10 and 12 in FIG. 2. The operation of the steps S18 and S20 is performed by the measurement unit 16 in FIG. 2.

First, in step S10, the stimulation timing control unit 14 inputs the delay times δa and δb. The delay times δa and δb may be input by an operator operating the information processing apparatus 44 and the information display system 24 or may be transferred over a network or the like.

Next, in step S12, the stimulation timing control unit 14 computes the start time t1s and the end time t1e of the stimulation S1, the start time t2s and the end time t2e of the stimulation S2 based on the delay times δa and δb as described in FIGS. 5 and 6. When multiple groups of the start time t1s, end time t1e, start time t2s, and end time t2e are acquired by calculation, the stimulation timing control unit 14 selects one of the following groups: the start time t1s, the end time t1e, the start time t2s, and the end time.

For example, the stimulation timing control unit 14 may select the times t1s, t1e, t2s, and t2e for maximizing the time intervals I1 and I2 among the multiple groups of the calculated times t1s, t1e, t2s, and t2e. In this case, the stimulation timing control unit 14 may maximize the time interval I1 and I2 so as to satisfy the minimum continuous time period of the stimulation S1 which makes the brain response to the stimulation S1 in the visual cortex continue for a predetermined time period and the minimum continuous time period of the stimulation S2 which makes the brain response to the stimulation S2 in the auditory cortex continue for a predetermined time period. Here, maximization means maximizing not only one of the time intervals I1 and I2 but also both of the time intervals I1 and I2.

The greater the time interval I1 and I2, respectively, the easier it is to distinguish the brain response to stimulation of interest from the brain response to stimulation out of interest. In addition, the desired measurement time can be secured by setting the minimum time for the stimulation S1 and S2 so that the brain response of each area to be measured continues for a predetermined time. As a result, a more conspicuous brain response can be accurately measured.

Further, the stimulation timing control unit 14 may display the multiple groups of the calculated times t1s, t1e, t2s, and t2e on the monitor display 28 of FIG. 1. An operator who operates the information processing apparatus 44 may select any of multiple groups of the times t1s, t1e, t2s, and t2e through an input device such as a mouse of the information display system 24 in the stimulation timing control unit 14. The stimulation timing control unit 14 may set the times t1s, t1e, t2s, and t2e selected by the operator or the like to the stimulation devices 10 and 12. Thus, the time t1s, t1e, t2s, and t2e can be selected based on the operator's intention to more clearly measure the brain response of the brain area of interest.

Next, in step S14, the stimulation timing control unit 14 sets the start time t1s and end time t1e of the stimulation S1 selected in step S12 to the stimulation device 10, and sets the start time t2s and end time t2e of the stimulation S2 to the stimulation device 12.

Next, in step S16, the stimulation device 10 outputs the stimulation S1 to the subject P according to the set start time t1s and end time t1e, and the stimulation device 12 outputs the stimulation S2 to the subject P according to the set start time t2s and end time t2e.

Next, in step S18, the measurement unit 16 measures a brain response (brain magnetic field) induced by the stimulation S1 and S2 in multiple brain areas of interest. Next, in step S20, when the measurement is continued to perform the summing average of the brain magnetic field data, for example, the measurement unit 16 returns the processing to step S14 and ends the measurement operation when a predetermined number of trials required for the summing average is performed. When the process returns to step S14, the stimulation timing control unit 14 preferably inserts a non-stimulation time of at least 300 ms.

Effects of the Invention

In accordance with the present invention, brain responses in different regions induced by stimulation in different organs can be accurately measured in a short time period.

Although the invention has been described in accordance with the embodiments, the invention is not limited to the requirements illustrated in the embodiments. In these respects, the subject matter of the present invention may be varied without prejudice and may be suitably defined according to its application.

Reference symbols are designated as follows:
1 Biomagnetic field measurement system
3 Measurement device.
5 Visual stimulation device
6 Auditory stimulation device
7 Air tube type earphone
10, 12 Stimulation device
14 Stimulation timing control unit
16 Measurement Department
22, 24 Information display system
26, 28 Monitor display
30 Dewar
31 Dent
42, 44 Information processing apparatus
61 CPU
62 RAM
63 ROM
64 Auxiliary memory device
65 I/O Interface
66 Display device
67 Bus
P Subject
t1s, t2s Start time
t1e, t2e End time
δa, δb Delay time

What is claimed is:

1. A brain response measurement system comprising:
a first stimulation output unit that applies first stimulation to a subject;
a second stimulation output unit that applies second stimulation to the subject;
a stimulation timing control unit that sets a timing of applying the first stimulation from the first stimulation output unit to the subject and the timing of applying the second stimulation from the second stimulation output unit to the subject; and
a measurement unit that measures a brain response occurring in a first brain area of the subject and a brain response occurring in a second brain area of the subject,
wherein a stimulation timing control unit calculates, based on a delay time δa from the brain response to the first stimulation in the first brain area to a brain response to the second stimulation in the first brain area, and a delay time δb from the brain response to the second stimulation in the second brain area to a brain response to the first stimulation in the second brain area, start and end times of the first stimulation and start and end times of the second stimulation that cause the brain response to the first stimulation in the first brain area and the brain response to the second stimulation in the first brain area not to overlap and cause the brain response to the second stimulation in the second brain area and the brain response to the first stimulation in the second brain are not to overlap, and
wherein the calculated start and end times of the first stimulation are set to the first stimulation output unit, and the calculated start and end times of the second stimulation are set to the second stimulation output unit.

2. The brain response measurement system according to claim 1,
wherein the stimulation timing control unit sets, when the start time of the first stimulation is referred to as t1s, the end time of the first stimulation is referred to as t1e, the start time of the second stimulation is referred to as t2s, and the end time of the second stimulation is referred to as t2e, a plurality of groups of the start time t1s, end time t1e, start time t2s, and end time t2e satisfying a relationship $(t1e-t2s)<\delta a$ and $(t2e-t1s)<\delta b$ are calculated, the calculated start time t1s and the end time t1e of any of the plurality of groups are set to the first stimulation output unit, and the calculated start time t2s and the end time t2e of any of the plurality of groups, are set to the second stimulation output unit.

3. The brain response measurement system according to claim 1,
wherein the stimulation timing control unit sets, when the start time of the first stimulation is referred to as t1s, the end time of the first stimulation is referred to as t1e, the start time of the second stimulation is referred to as t2s, and the end time of the second stimulation is referred to as t2e, a plurality of groups of the start time t1s, end time t1e, start time t2s, and end time t2e satisfying the relationship (t1e−t2s)<50 ms and (t2e−t1s)<50 ms are calculated, the calculated start time t1s and the end time t1e of any of the plurality of groups are set to the first stimulation output unit, and the calculated start time t2s and the end time t2e of any of the plurality of groups are set to the second stimulation output unit.

4. The brain response measurement system according to claim 2,
wherein the stimulation timing control unit respectively sets the start time t1s, the end time t1e, the start time t2s, and the end time t2e to the first stimulation output unit and the second stimulation output unit, the start time tis, the end time t1e, the start time t2s, and the end time t2e maximizing a first time interval from the end time of the brain response in the first brain area caused by the first stimulation to the start time of the brain, response in the first brain area caused by the second stimulation and the second time interval from the end time of the brain response in the second brain area caused by the second stimulation to the start time of the brain response in the second brain area caused by the first stimulation.

5. The brain response measurement system according to claim 4,
wherein the stimulation timing control unit sets the start time t1s, the end time t1e, the start time t2s, and the end time t2e maximizing the first time interval and the second time interval so as to satisfy a minimum continuous time period while the first stimulation is acquired continuously for a predetermined time period by the first stimulation and a minimum continuous time period while the second stimulation is acquired continuously for a predetermined time period by the second stimulation.

6. The brain response measurement system according to claim 2,
wherein the stimulation timing control unit displays the calculated start time t1s and the end time t1e of the plurality of groups and the calculated start time t2s and the end time t2e of the plurality of, groups on a display device, and set the start time t1s, end time t1e, start time t2s, and end time t2e selected through an input device to the first and second stimulation output units, respectively.

7. The brain response measurement system according to claim 1,
wherein the stimulation timing control unit sets cycle periods of the first stimulation and the second stimulation to be at least 300 ms, and randomly changes the cycle period within a predetermined time range every time the first stimulation or the second stimulation is given.

8. The brain response measurement system according to claim 1,
wherein the stimulation timing control unit sets the start time t1s of the first stimulation and the start time t2s of the second stimulation to be a same time.

9. The brain response measurement system according to claim 1,
wherein the stimulation timing control unit calculates the start time and the end time of the first stimulation and the start time and the end time of the second stimulation based on the delay time δa and the delay time δb, which are determined in accordance with a type of the stimulation and/or characteristics of the subject.

10. The brain response measurement system according to claim 1,
wherein the stimulation timing control unit outputs, by the first stimulation output unit, synchronization information indicating a timing when the subject receives the first stimulation based on the delay time from when the first stimulation is output to the subject until when the subject receives the first stimulation, and
wherein a measurement unit recognizes a time when the subject actually receives the first stimulation based on the synchronization information and associates the recognized time with the measured data of brain response of the first brain area.

11. The brain response measurement system according to claim 1,
wherein the stimulation timing control unit outputs, by the second stimulation output unit, synchronization information indicating a timing when the subject receives the second stimulation based on the delay time from when the second stimulation is output to the subject until when the subject receives the second stimulation, and
wherein a measurement unit recognizes a time when the subject actually receives the second stimulation based on the synchronization information and associates the recognized time to the measured data of brain response of the second brain area.

12. The brain response measurement system according to claim 1,
wherein the first stimulation is any of a visual stimulation, an auditory stimulation, or a somatic sensation stimulation, and
wherein the second stimulation, is any of the visual stimulation, the auditory stimulation, or the somatic sensation stimulation, the second stimulation being different from the first stimulation.

13. The brain response measurement system according to claim 1,
wherein the first stimulation is a visual stimulation or an auditory stimulation, and
wherein the second stimulation is the visual stimulation or the auditory stimulation, the second stimulation being different from the first stimulation.

14. The brain response measurement system according to claim 1,
wherein the measurement unit measures a brain magnetic field generated by a response occurring in a brain of the subject.

15. A brain response measurement method of measuring a brain response by a brain response measurement system including
a first stimulation output unit that applies a first stimulation to a subject,
a second stimulation output unit that applies a second stimulation to the subject,
a stimulation timing control unit that sets a timing of applying the first stimulation from the first stimulation output unit to the subject and a timing of applying the second stimulation from the second stimulation output unit to the subject, and a measurement unit that measures a brain response to the first stimulation in a first brain area of the subject and a brain response to the second stimulation in a second brain area of the subject;

the brain response measurement method, comprising:

calculating, by the stimulation timing control unit, start and end times of the first stimulation and start and end times of the second stimulation that cause the brain response to the first stimulation in the first brain area and the brain response to the second stimulation in the second brain area not to overlap and cause the brain response the second stimulation in the second brain area and a brain response to the first stimulation in the second brain area not to overlap, based on a delay time δa of a brain response to, the second stimulation in the first brain area to the brain response to the first stimulation in the first brain area, and a delay time δb of the brain response to the first stimulation in the second brain area to the brain response to the second stimulation in the second brain area; and setting the calculated start and end times of the first stimulation to the first stimulation output unit and the calculated start and end times of the second stimulation to the second stimulation output unit.

16. A computer program embodied in a non-transitory computer-readable medium and representing a sequence of instructions, which when executed by a computer included in a brain response measurement system that includes a first stimulation output unit that applies a first stimulation to a subject, a second stimulation output unit that applies a second stimulation to the subject, a stimulation timing control unit that sets a timing of applying the first stimulation from the first stimulation output unit to the subject and a timing of applying the second stimulation from the second stimulation output unit to the subject, and a measurement unit that measures a brain response to the first stimulation in a first brain area of the subject and a brain response to the second stimulation in a second brain area, of the subject, the instructions cause the computer to perform steps of:

calculating, by the stimulation timing control unit, start and end times of the first stimulation and start and end times of the second stimulation that cause the brain response to the first stimulation in the first brain area and the brain response to the second stimulation in the second brain area not to overlap and cause the brain response the second stimulation in the second brain area and, a brain response to the first stimulation in the second brain area not to overlap, based on a delay time δa of a brain response to, the second stimulation in the first brain area to the brain response to the first stimulation in the first brain area, and a delay time δb of the brain response to the first stimulation in the second brain area to the brain response to the second stimulation in the second brain area; and setting the calculated start and end times of the first stimulation to the first stimulation output unit and the calculated start and end times of the second stimulation to the second stimulation output unit.

* * * * *